(12) United States Patent
Jones et al.

(10) Patent No.: US 7,094,736 B2
(45) Date of Patent: Aug. 22, 2006

(54) SAMPLING OF HYDROCARBONS FROM GEOLOGICAL FORMATIONS

(75) Inventors: Timothy Gareth John Jones, Cottenham (GB); Gary John Tustin, Sawston (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 388 days.

(21) Appl. No.: 10/451,856

(22) PCT Filed: Feb. 1, 2002

(86) PCT No.: PCT/GB02/00448

§ 371 (c)(1),
(2), (4) Date: Jan. 2, 2004

(87) PCT Pub. No.: WO02/063295

PCT Pub. Date: Aug. 15, 2002

(65) Prior Publication Data

US 2004/0106524 A1    Jun. 3, 2004

(30) Foreign Application Priority Data

Feb. 7, 2001  (GB) ................................. 0103004.8

(51) Int. Cl.
*C12S 13/00* (2006.01)
*C09K 8/035* (2006.01)
*C09K 8/34* (2006.01)
*C09K 8/502* (2006.01)

(52) U.S. Cl. .................. 507/103; 507/203; 507/101; 507/201; 507/116; 507/218

(58) Field of Classification Search ............. 507/100, 507/101, 103, 110, 116, 200, 201, 203, 209, 507/218
See application file for complete search history.

(56) References Cited

U.S. PATENT DOCUMENTS

| | | |
|---|---|---|
| 3,369,345 A | 2/1968 | Moore et al. |
| 4,174,629 A | 11/1979 | Striegler |
| 4,936,139 A | 6/1990 | Zimmerman et al. |
| 5,165,477 A | 11/1992 | Shell et al. |
| 5,232,910 A | 8/1993 | Mueller et al. |
| 5,252,554 A | 10/1993 | Mueller et al. |
| 5,725,771 A | 3/1998 | Aliphat et al. |
| 5,881,813 A | 3/1999 | Brannon et al. |
| 6,232,274 B1 | 5/2001 | Hughes et al. |

FOREIGN PATENT DOCUMENTS

| | | | |
|---|---|---|---|
| GB | 2 324 322 A | 10/1998 | |
| GB | 2 332 223 B | 1/2000 | |
| WO | 92/15771 A1 | 9/1992 | |

OTHER PUBLICATIONS

Akram et al A model to predict wireline formation tester sample contamination SPE Reservoir Evaluation & Engineering, vol. 2, No. 6, 1999, pp. 499-505.
Almond et al Utilization of biologically generated acid for drilling fluid damage removal and uniform acid placement across long formation intervals European Formation Damage Conference, The Hague, May 15-16, 1995, SPE 30123.
Anderson et al The hydrolysis of p-nitrophenyl acetate: a versatile reaction to study enzyme kinetics Journal of Chemical Education, vol. 71, No. 8, 1994, pp. 715-718.
Atanasov et al Environmental biosensors based on mediatorless bioelectrocatalysis 217th ACS National Meeting, Anaheim, CA, Mar. 21-25, 1999, pp. 486-487.
Badry et al New wireline formation tester techniques and applications SPWLA 34th Annual Logging Symposium, Calgary, Jun. 1993, paper zz.
Brown et al Synthetic base fluids Chemistry and Technology of Lubricants (Mortier and Orszulik eds.), second edition, Blackie Academic & Professional, London 1997, pp. 34-41.
Carlson et al Meeting the challenges of deepwater Gulf of Mexico drilling with non-petroleum ester-based drilling fluids SPE International Petroleum Conference, Veracruz, Mexico, Oct. 10-13, 1994, SPE 28739.
Churan et al Onsite and offsite monitoring of synthetic-based drilling fluids for oil contamination SPE/EPA Exploration and Production Environmental Conference, Dallas, Mar. 3-5, 1997, SPE 37906.
Curiale et al Occurrence and origin of olefins in crude oils. A critical review. Organic Geochemistry, vol. 29, No. 1, 1998, pp. 397-408.
Felling et al Characterization of in-situ fluid responses using optical fluid analysis SPE Annual Technical Conference and Exhibition, San Antonio, Oct. 5-8, 1997, SPE 38649.

(Continued)

*Primary Examiner*—Randy Gulakowski
*Assistant Examiner*—Timothy J. Kugel
(74) *Attorney, Agent, or Firm*—Steven Gahlings; Jody Lynn DeStefanis; William L. Wang

(57) ABSTRACT

A method of separating from a mixture of oil-based drilling fluid and sample of formation hydrocarbon, the liquid component of the drilling fluid, which method comprises treating, e.g. chemically, the mixture in a way that selectively substantially affects the liquid component of the drilling fluid, producing one or more treatment products, while leaving the formation hydrocarbon substantially unaffected; and separating the treatment products from the formation hydrocarbon, by solvent extraction. The liquid component of the drilling fluid conveniently comprises one or more esters (which do not occur in significant quantities in naturally occuring formation hydrocarbons) and which can be hydrolysed to give water-soluble products readily removable from the formation hydrocarbon. The invention is applicable to sampling of formation hydrocarbon using wireline formation testers or sampling tools.

13 Claims, No Drawings

OTHER PUBLICATIONS

Fernandez-Lafuente et al Immobilization of lipases by selective adsorption on hydrophobic supports Chemistry and Physics of Lipids, vol. 93, 1998, pp. 185-197.

Friedheim et al Second generation synthetic fluids in the North Sea: are they better? IADC/SPE Drilling Conference, New Orleans, Mar. 12-15, 1996, SPE 35061.

Friedheim et al Superior performance with mineral environmental impact: a novel nonaqueous drilling fliud IADC/SPE Drilling Conference, Amsterdam Feb. 23-25, 1993, SPE 25753.

Furniss et al Practical organic chemistry Vogel's Textbook of Practical Organic Chemistry, 5th edition, Longman Scientific and Technical, 1989, p. 158.

Hammond One- and two-phase flow during fluid sampling by a wireline tool Transport in Porous Media, vol. 6, 1991, pp. 299-330.

Hanssen et al New enzyme process for downhole cleanup of reservoir drilling fluid filtercake SPE International Symposium on Oilfield Chemistry, Houston, Feb. 16-19, 1999, SPE 50709.

Harris et al New applications for enzymes in oil and gas production SPE European Petroleum Conference, The Hague, Oct. 20-22, 1998, SPE 50621.

Hashem et al Determination of producible hydrocarbon type and oil quality in wells drilled with synthetic oil-based muds SPE Reservoir Evaluation & Engineering, 2(2), 1999, pp. 125-133.

Heiss et al Polyethylene glycol monomethyl ether-modified pig liver esterase: preparation, characterization and catalysis of enantioselective hydrolysis in water and acylation in organic solvents Tetrahedron Letters, vol. 36, No. 22, 1995, pp. 3833-3836.

Jacques et al A comparison of field drilling experience with low-viscosity mineral oil and diesel muds IADC/SPE Drilling Conference, New Orleans Feb. 18-21, 1992, SPE 23881.

Kenny Ester-based muds show promise for replacing some oil-based muds Oil & Gas Journal, vol. 91, No. 45, 1993, pp. 88-91.

Kinnear et al Direct electron transfer to *Escherichia coli* fumarate reductase in self-assembled alkanethiol monolayers on gold electrodes Langmuir, 9, 1993, pp. 2255-2257.

Larter et al Reservoir geochemistry: methods, applications and opportunities The Geochemistry of Reservoirs (J.M. Cubitt and W.A. England eds.), Geological Society Special Publication No. 86, The Geological Society, London 1995, pp. 5-32.

Mar. Aliphatic nucleophilic substitution Advanced Organic Chemistry, 4th edition, Wiley-Interscience, New York, 1992, pp. 336-340.

Morris et al Using optical fluid analysis to evaluate downhole fluid sample contamination SPE European Petroleum Conference, The Hague, Oct. 20-22, 1998, SPE 50603.

Munro et al Biodegradation of base fluids used in synthetic drilling muds in a solid-phase test SPE/UKOOA European Environmental Conference, Aberdeen Apr. 15-16, 1997, SPE 37861.

Nicolle et al Geochemistry: a powerful tool for reservoir monitoring Middle East Oil Show, Bahrain, Mar. 15-18, 1997, SPE 37804.

Proett et al New wireline formation testing tool with advanced sampling technology SPE Annual Technical Conference, Houston, Oct. 3-6, 1999, SPE 56711.

Rissom et al Asymmetric reduction of acetophenone in membrane reactors: comparison of oxazaborolidine and alcohol dehydrogenase catalysed processes Tetrahedron: Asymmetry, 10, 1999, pp. 923-928.

Schlumberger Sampling Wireline formation testing and sampling, Houston, Texas, 1996, pp. 10-1 to 10-25.

Shubkin Polyalphaolefins Synthetic Lubricants and High-Performance Functional Fluids (Shubkin ed.), Marcel Dekker, Inc., New York, 1992, pp. 1-7.

Smits et al In-situ optical fluid analysis as an aid to wireline formation sampling SPE Formation Evaluation, 10, Jun. 1995, pp. 91-98.

Sousa et al Asymmetric hydrolysis of a meso-diester using pig liver esterase immobilised in hollow fibre ultrafiltration membrane Tetrahedron: Asymmetry 11, 2000, pp. 929-934.

Underhill et al Model-based sticking risk assessment for wireline formation testing tools in the US Gulf Coast SPE Annual Technical Conference, New Orleans Sep. 27-30, 1998, SPE 48963.

SAMPLING OF HYDROCARBONS FROM GEOLOGICAL FORMATIONS

FIELD OF INVENTION

This invention concerns sampling of hydrocarbons from geological formations.

BACKGROUND TO THE INVENTION

During exploration of a geological formation bearing oil and/or gas (hydrocarbon), and during development and management of extraction of hydrocarbon therefrom, it is important to be able to obtain representative samples of hydrocarbon from the formation. It is known to do this using a down hole wireline formation testers or sampling tools such as the Modular Dynamics Formation Tester (MDT) tool of Schlumberger. For a description of such equipment see Badry, R., Head, E., Morris, C. and Traboulay. I., "New wireline formation tester techniques and applications", *Trans. SPWLA* 34$^{th}$ *Ann. Logging Symp.*, Calgary, June 1993, paper ZZ, and Schlumberger, *Wireline Formation Testing and Sampling*, pp. 10-1 to 10-25, Schlumberger Wireline and Testing, Houston (1996). The MDT tool allows samples of hydrocarbon to be captured and maintained at reservoir pressure in sealed containers. The samples are recovered at the surface and analysed to determine their composition (in terms of the relative amounts of different hydrocarbons) and their phase (pressure-volume-temperature or PVT) behaviour.

The acquisition of representative hydrocarbon samples from permeable formations can be impeded by several problems.

A major difficulty that commonly occurs when sampling is contamination by invasion of significant quantities of drilling fluid. This is particularly the case when using oil-based drilling fluids (also known as oil-based muds or OBMs). The base oil in OBMs usually consists of refined mineral oil, unrefined diesel oil or so-called synthetic oil such as poly(alphaolefins) or esters derived from vegetable oils. The OBM further comprises suspended solids in the form of weighting agent (commonly barite), fluid loss control agent (commonly clay) and possibly also drilled solids generated during drilling. The continuous liquid component of OBMs (the filtrate) is completely miscible with the formation hydrocarbons, and it is difficult to distinguish the filtrate from the formation hydrocarbons. This frequently results in samples of formation hydrocarbon contaminated with filtrate being collected. Such contamination results in inaccurate composition and phase behaviour information being obtained.

Another consideration is the length of sampling time. While sampling times may be prolonged with the aim of initially pumping out drilling fluid and contaminated formation hydrocarbon, thus reducing the likelihood of obtaining contaminated samples, longer sampling times increase the risk of the sampling tool and/or cable sticking in the hole. The sticking can be caused by the difference in the pressures in the drilling fluid column and permeable formations (so-called differential sticking) or by the condition or the geometry of the hole (key seating, swelling/collapsing shale sections etc). There is therefore a direct conflict between the need for extended sampling times to reduce sample contamination and the need for short sampling times to reduce the risk of sticking.

SUMMARY OF THE INVENTION

In one aspect, the invention provides a method of separating from a mixture of oil-based drilling fluid (OBM) and a sample of formation hydrocarbon, the liquid component of the drilling fluid (filtrate), which method comprises treating the mixture in a way that selectively substantially affects the liquid component of the drilling fluid, producing one or more treatment products, while leaving the formation hydrocarbon substantially unaffected; and separating the treatment product(s) from the formation hydrocarbon.

In a further aspect, the invention provides a method of recovering a sample of hydrocarbon from a formation, comprising drilling a bore hole into the formation using an oil-based drilling fluid; extracting into the bore hole a sample of fluid comprising hydrocarbon from the formation, possibly mixed with the oil-based drilling fluid; treating the sample in a way that selectively substantially affects and, preferentially, selectively affects only, the liquid component of the drilling fluid, producing one or more treatment products, while leaving the formation hydrocarbon substantially unaffected; and removing the treatment product(s) to leave a substantially uncontaminated sample of hydrocarbon from the formation.

DETAILED DESCRIPTION OF THE PREFERRED EMBODIMENTS

The invention requires use of a suitable drilling fluid that yields treatment product or products, which are distinguishable from, and separable from, the formation hydrocarbon. The drilling fluid must thus be capable of being selectively and differentially treated, to be distinguishable from the formation hydrocarbon.

The treatment step typically involves conversion of the liquid component of the drilling fluid into two or more products, distinguishable from the formation hydrocarbon.

The treatment step may involve one or more stages.

Typically, the treatment step involves chemical treatment of the mixture. In this case, the drilling fluid must be chemically distinct from the formation hydrocarbon.

The chemical treatment preferably involves a catalytic reaction, conveniently catalysed by an enzyme or other similar bio-catalyst. Enzymes (and similar bio-catalysts) have the advantage of often catalysing only very specific reactions, enabling targeting of the treatment to the drilling fluid only. Enzyme-catalysed reactions may also occur more rapidly and/or under milder conditions than would otherwise be the case. Where an enzyme is used, this is desirably in immobilised condition, typically immobilised on a solid support in known manner. Use of an enzyme in immobilised condition enables ready control of the location where the enzyme-catalysed reaction occurs, by appropriate positioning of the enzyme, thus assisting the design of processing equipment. Further, immobilisation of enzymes is known to improve the thermal stability of enzymes and protect them to an extent from denaturation that is otherwise frequently observed at high temperatures, with consequent benefits in the case of treatment performed down hole in a wire sampling tool where conditions of high temperature and pressure are likely to prevail. Enzymes derived from extromophiles may provide robust catalysts able to function under extreme conditions of pressure and temperature possibly encountered by a wireline sampling tool.

In one preferred embodiment, the liquid component of the drilling fluid comprises one or more esters. Esters do not occur in any significant quantities in naturally occuring formation hydrocarbons, and esters are thus chemically distinct from the ingredients of formation hydrocarbons. In this case, the treatment step conveniently comprises hydrolysis of the ester to yield an alcohol and an acid, while leaving the formation hydrocarbon unaffected. Hydrolysis of an ester can be carried out under acidic or basic conditions as appropriate depending on the ester, or can be performed enzymically. The products of hydrolysis, possibly after further chemical treatment of the alcohol component, are generally water-soluble, and so can be readily separated from the formation hydrocarbon, eg by solvent extraction.

It is particularly preferred to use an enzyme-catalysed reaction because of the specificity and other benefits mentioned above; suitable esterases for hydrolysis of esters are well-known and commercially available. For example, exposure of a mixture of crude oil and ester to immobilised pig liver esterase (PLE) (eg as described in Heiss, L., Gais, H-S., "Polyethylene glycol monomethyl ether-modified pig liver esterase: preparation, characterization and catalysis of enantioselective hydrolysis in water and acylation in organic solvents", *Tetrahedron Lett.*, 36, 3833, (1995) and references cited therein) will result in a mixture of crude oil, alcohol and acid. The latter two components are readily removed by aqueous extraction and, as natural crude oils do not contain esters, no components of the reservoir hydrocarbon sample are lost in this process.

The generalised structure of some aliphatic esters for possible use in synthetic oil-based drilling fluids is as follows:

ther, the acid and/or alcohol component may include one or more positions of unsaturation. The ester should be selected to have suitable properties for functioning as a drilling fluid, in terms of chemical stability etc, as is well known in the art. Mixtures of esters may be used.

As mentioned above, it is known to use esters in oil-based drilling fluids. The esters currently used in drilling muds usually contain a straight chain attached to a branched alcohol. The branching makes the esters more difficult to hydrolyse under normal conditions, providing stability in use. These esters can be hydrolysed under appropriate conditions, e.g. using enzymes, but the resulting alcohol will usually be sparingly soluble in water. For example, U.S. Pat. No. 5,232,910 discloses one drilling fluid comprising isobutyl rape-seed oil ester, and another drilling fluid comprising oleic acid isobutyl ester, and U.S. Pat. No. 5,252,554 discloses a drilling fluid comprising lauric acid/n-hexyl ester. Such esters can be used in the method of the invention.

The acid product of hydrolysis of an ester is generally highly water-soluble when in the form of a salt.

The alcohol product of hydrolysis of an ester may be only sparingly soluble in water, as is the case with longer and/or branched chain alcohols. In this event, it may be necessary or appropriate further to treat the alcohol, eg. by enzymic or chemical oxidation, to produce the corresponding acid, to give a water soluble product for ease of separation.

An example of a typical two-stage treatment step of this sort is as follows:

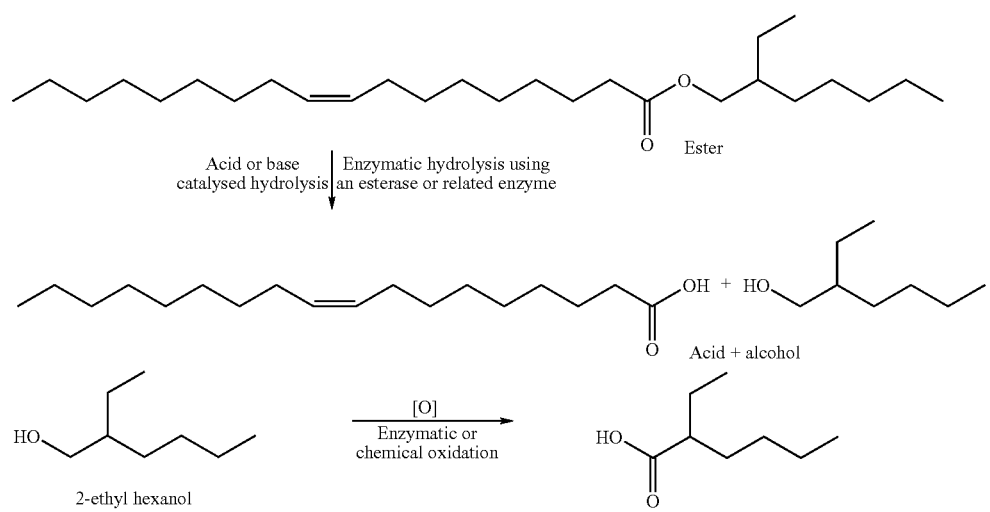

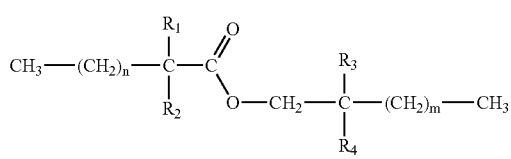

A wide range of esters satisfying this general formula may be used, with a range of different chain lengths (indicated by n and m), with straight chains ($R_1$ and $R_2$=H) or branched chains for the acid component and/or straight chains ($R_3$ and $R_4$=H) or branched chains for the alcohol component. Fur- It may be preferred to use an ester having a short chain (branched or linear) alcohol component (e.g. iso-butanol rather than 2-ethyl hexanol as in the reaction scheme above) to yield a water-soluble alcohol on hydrolysis.

A further possibility is to use esters in which the acid component is branched, with the alcohol component being branched or linear, as this will allow the use of shorter chain esters which are resistant to hydrolysis under normal drilling conditions yet which hydrolyse (e.g. on exposure to a suitable esterase) to yield two, small water soluble species, readily separable from formation hydrocarbon. The use of α-branched carboxylic acids, branched at the a carbon adjacent to the carbon of the carbonyl group, for example, may confer some advantages.

It is well known that the esters formed from α-branched carboxylic acids exhibit marked resistance to alkaline hydrolysis. The increased hydrolytic stability of esters formed with α-branched carboxylic acids may enable lower molecular weight acids to be used and with a subsequent reduction in the viscosity of the drilling fluid.

In the method of the invention it is thus proposed particularly to use an ester of an α-branched acid, preferably with a linear alcohol. Such esters have good stability to hydrolysis under typical down-hole conditions of use, yet are hydrolysable under appropriate conditions to yield water-soluble products. The α-branched acid is preferably relatively short-chained, having up to 12 carbon atoms. This approach also has the added advantage of increasing the water solubility of the acid salt generated compared to that of the non-branched acid. The example shown below is of 2-methyl oleic acid-methyl ester.

It may be convenient to use a mixture of esters, eg based on naturally occurring vegetable oils having a range of different acid components of different chain length.

The liquid component of the drilling fluid may alternatively or additionally comprise other hydrolysable chemical species, eg amides, acetals and ortho-esters. Non-hydrolysable chemical species may alternatively be used, eg poly(alphaolefins). Poly(alphaolefins) are hydrocarbons manufactured by catalytic oligomerization of linear α-olefins having six or more, usually 10 carbon atoms. Poly(alphaolefins) have terminal unsaturation not generally found in significant quantities in naturally occurring hydrocarbons present in formation hydrocarbon. Terminal double bonds of the form —CH=CH$_2$ have been identified in some crude oils (see Curiale, J. A. and Frolov, E. B., "Occurrence and origins of olefins in crude oils. A critical review", *Organic Geochemistry*, 29, 397-408 (1998)). The olefin content of

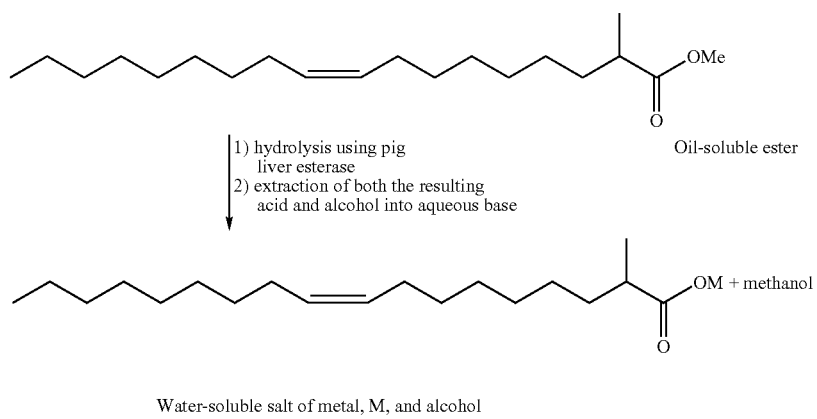

A further possible approach is to use esters of polyols such as diols and triols. The use of a triglyceride as an ester for drilling muds has not previously been proposed. These compounds are extremely hydrophilic and hydrolytically stable. They can, however, be hydrolysed e.g. by porcine pancreatic lipase (see Faber, K *Biotransformations in Organic Chemistry*, 3$^{rd}$ edition, 1996, and references cited therein) to give a highly water soluble triol and acid. This reaction is facilitated using biphasic media. An example is illustrated below.

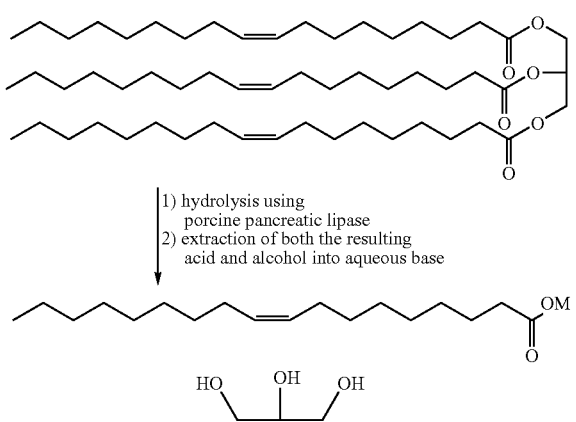

crude oils is typically in the range 0.02–10 weight percent, although this upper concentration is rarely achieved, and 1–2 weight percent is more common. Generally the olefin content of a crude oil increases as the age of the reservoir increases. The terminal olefin content of most crude oils is low and the loss of these olefins during the extraction of olefin-based drilling fluid will generally have a negligible effect on the phase behaviour or composition of the crude oil sample. The separated treatment products can be analysed to identify the presence of any compounds derived from olefins originally in the crude oil sample. If an abnormally high content of naturally-occurring terminal olefins in the reservoir hydrocarbon samples is suspected before sampling, an ester- or other non-olefin-based oil can be used in the drilling fluid. With all such drilling fluids, the treatment step must in each case be suitably tailored to yield one or more products separable from the formation hydrocarbon.

For example, with poly(alphaolefins) an enzymic or other chemical process may be used that converts such compounds to water-soluble materials. For a discussion of enzymic processes, see the Faber reference mentioned above. For other chemical approaches see March, J., *Advanced Organic Chemistry*, 4$^{th}$ edition, pp. 336–340, Wiley-Interscience, New York (1992). Options for this process include oxidative-cleavage of the olefins and subsequent further oxidation to the corresponding diol or carboxylic acid, both of which are soluble in aqueous media.

This approach could be achieved using a variety of reaction schemes. Two possible routes are shown schematically below:

products of hydrolysis of esters, as discussed above, may be extracted in known manner into a mixture of water and alcohol.

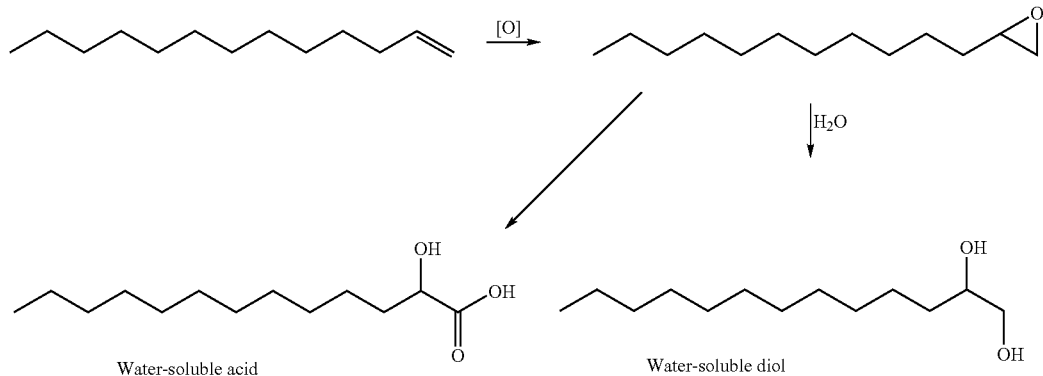

With this approach it is important to note that the terminal double bonds found only in the drilling fluid filtrate can be distinguished from the non-terminal double bonds found in the naturally-occurring hydrocarbons in oil samples.

Amides, acetals and ortho-esters are functionalities that can be hydrolysed to give alcohols and polar functionalities, which are usually water soluble. Chemical or enzymatic hydrolysis of these molecules gives products that can be extracted into aqueous media. An example is shown below for an ortho-ester.

The invention is applicable to sampling of formation hydrocarbon using wireline formation testers or sampling tools such as Schlumberger's MDT tool, as discussed above. The tool is used in conventional manner to obtain a sample of what is believed to be formation hydrocarbon, possibly contaminated with oil-based drilling fluid. Suspended solids will generally be initially removed in conventional manner, usually by physical filtration methods, to leave the formation hydrocarbon possibly mixed with drilling fluid filtrate. By processing this mixture by the method of the invention, the

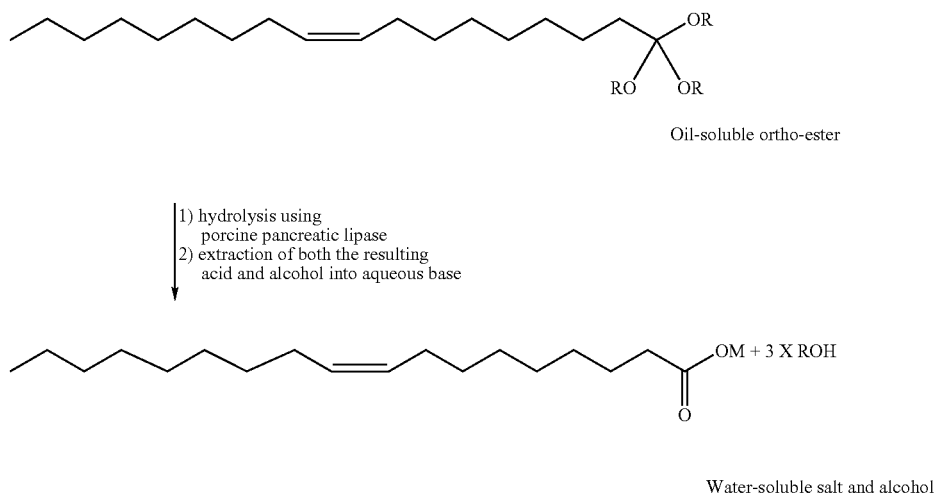

The separation step conveniently uses a physical separation technique. Appropriate techniques can be readily determined and selected having regard to the nature and properties of the treatment product or products. One convenient separation technique is solvent extraction. Where the treatment product or products are water soluble, as discussed above, they can be readily removed from the water-insoluble formation hydrocarbon in the mixture under treatment, by extraction into water in known manner. Solvent extraction using other solvents or mixtures of solvents may be adopted in some cases: for example, poorly water-soluble alcohol filtrate, if present, can be removed, leaving a substantially pure sample of formation hydrocarbon ready for analysis.

The processing by the method of the invention can be performed in situ in the tool under downhole conditions or at the surface under less demanding conditions, eg in a laboratory.

On-line sensors can be used to monitor the process. For example, the optical fluid analyser (OFA) of the tool can be used to monitor the process in the wireline sampling tool, or a similar spectrometer or other sensor can be used to monitor the process in a laboratory. An on-line sensing device will allow the changes in the mixture to be monitored before and after treatment and separation. This continual treatment/separation/monitoring process will allow the clean-up process to be carried out at an optimal rate, and by monitoring the process it is possible to determine when the clean-up process is complete. When the sensor has determined that there is no further change in the composition of the mixture, this indicates that the clean-up process is complete; the formation hydrocarbon sample can then be considered as contaminant free.

The ability to remove contaminating drilling fluid filtrate from a formation hydrocarbon sample obviates the need for extended sampling times, thereby reducing the risk of tool sticking.

In a further aspect, the invention provides a method of recovering a sample of hydrocarbon from a formation, comprising drilling a bore hole into the formation using an oil-based drilling fluid; extracting into the bore hole a sample of fluid comprising hydrocarbon from the formation, possibly mixed with the oil-based drilling fluid; treating the sample in a way that selectively substantially affects and, preferentially, selectively affects only, the liquid component of the drilling fluid, producing one or more treatment products, while leaving the formation hydrocarbon substantially unaffected; and removing the treatment product(s) to leave a substantially uncontaminated sample of hydrocarbon from the formation.

Sample extraction is conveniently carried out using a downhole wireline formation tester or sampling tool such as a MDT tool from Schlumberger.

The invention will be further described, by way of illustration, in the following Example.

EXAMPLE

A mixture of formation hydrocarbon and the oil-soluble ester iso-butyl oleate was prepared to simulate a sample of hydrocarbon contaminated with oil-based drilling fluid filtrate comprising iso-butyl oleate. The mixture was circulated over a surface bearing immobilised esterase, eg pig liver esterase as referred to above. This results in hydrolysis of the ester to give oleic acid and isobutanol, while leaving the formation hydrocarbon unaffected. The mixture was then contacted with a slightly basic aqueous solution (containing potassium carbonate, for example), into which dissolve the water-soluble alcohol iso-butanol, and the water soluble metal salt of the oleic acid. The aqueous solution is separated from the immiscible formation hydrocarbon, leaving a sample of formation hydrocarbon free from contamination. The process is illustrated in the following reaction scheme:

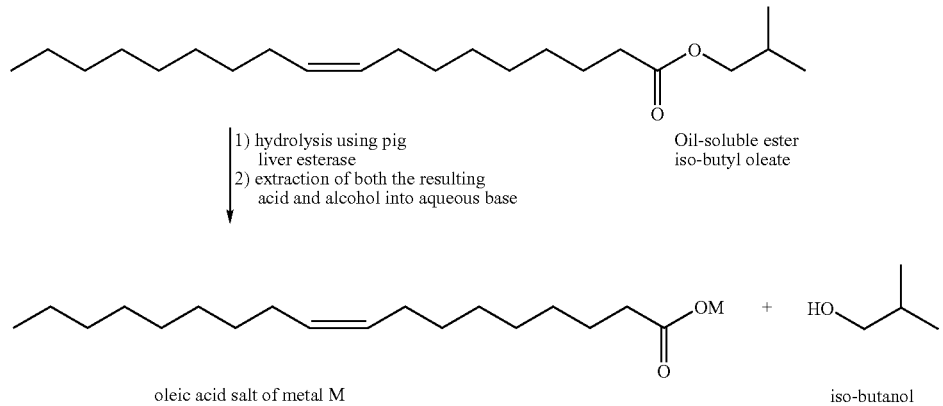

This approach can be applied during extraction of hydrocarbon samples from a formation, eg by using a Schlumberger Modular Dynamics Formation Tester (MDT) tool, using an oil-based drilling fluid in which the oil is iso-butyl oleate.

The hydrolysis/separation process can be performed in the wireline sampling tool at reservoir conditions, or in a laboratory at ambient temperature. On-line sensors can be used to monitor the process. For example, the optical fluid analyser (OFA) of the tool can be used to monitor the process in the wireline sampling tool, or a similar spectrometer or other sensor can be used to monitor the laboratory process. An on-line sensing device will allow the changes in the mixture to be monitored before and after contact with the immobilised enzyme. This continual extraction/monitoring process will allow the clean-up process to occur at an optimal rate and this process can be monitored to determine when the process is complete. When the sensor has determined that the process is complete (i.e., there is no further change is the composition of the mixture), the sample can then be considered as contaminant free.

The invention claimed is:

1. A method of separating from a mixture of oil-based drilling fluid and a sample of formation hydrocarbon, the liquid component of the drilling fluid, which method comprises chemically treating the mixture in a way that selectively substantially affects the liquid component of the drilling fluid, producing one or more treatment products, while leaving the formation hydrocarbon substantially unaffected; and separating the one or more treatment products from the formation hydrocarbon.

2. A method according to claim 1, wherein the chemical treatment involves an enzyme-catalysed reaction.

3. A method according to claim 2, wherein the enzyme is in immobilised condition.

4. A method according to any one of the preceding claims, wherein the liquid component of the drilling fluid comprises one or more esters.

5. A method according to claim 4, wherein the drilling fluid comprises an ester of an α-branched acid.

6. A method according to claim 4 or claim 5, wherein the treatment step comprises hydrolysis of the ester to yield an alcohol and an acid.

7. A method according to any one of the preceding claims, wherein the liquid component of the drilling fluid comprises poly(alphaolefins).

8. A method according to claim 7, wherein the treatment step comprises one or more oxidations of the poly(alpha-olefins) in order to obtain diols or carboxylic acids.

9. A method according to claim 8, wherein the one or more oxidations are done enzymatically or chemically.

10. A method according to anyone of the preceding claims, wherein the separation step uses a physical separation technique.

11. A method according to claim 10, wherein the separation stop comprises solvent extaction.

12. A method of recovering a sample of hydrocarbon from a formation, comprising drilling a bore hole into the formation using an oil-based drilling fluid; extracting into the bore hole a sample of fluid comprising hydrocarbon from the formation, possibly mixed with the oil-based drilling fluid; chemically treating the sample in a way that selectively substantially affects the liquid component of the drilling fluid, producing one or more treatment products, while leaving the formation hydrocarbon substantially unaffected; and removing the one or more treatment products to leave a substantially uncontaminated sample of hydrocarbon from the formation.

13. A method according to claim 12, wherein sample extraction is carried out using a downhole wireline formation tester or sampling tool.

* * * * *